United States Patent
Schulze zur Wiesche et al.

(10) Patent No.: US 10,857,081 B2
(45) Date of Patent: Dec. 8, 2020

(54) STABLE COLOR-PROTECTING HAIR TREATMENT AGENT COMPRISING LANTHANIDE SALT

(71) Applicant: Henkel AG & Co. KGaA, Dusseldorf (DE)

(72) Inventors: Erik Schulze zur Wiesche, Hamburg (DE); Rene Krohn, Norderstedt (DE)

(73) Assignee: Henkel AG & Co. KGaA, Dusseldorf (DE)

( * ) Notice: Subject to any disclaimer, the term of this patent is extended or adjusted under 35 U.S.C. 154(b) by 0 days.

(21) Appl. No.: 15/619,814

(22) Filed: Jun. 12, 2017

(65) Prior Publication Data

US 2017/0360663 A1    Dec. 21, 2017

(30) Foreign Application Priority Data

Jun. 16, 2016   (DE) ........................ 10 2016 210 809

(51) Int. Cl.
| | |
|---|---|
| *A61K 8/19* | (2006.01) |
| *A61K 8/362* | (2006.01) |
| *A61K 8/365* | (2006.01) |
| *A61K 8/368* | (2006.01) |
| *A61K 8/42* | (2006.01) |
| *A61K 8/44* | (2006.01) |
| *A61K 8/46* | (2006.01) |
| *A61K 8/60* | (2006.01) |
| *A61K 8/86* | (2006.01) |
| *A61K 8/894* | (2006.01) |
| *A61K 8/92* | (2006.01) |
| *A61Q 5/00* | (2006.01) |
| *A61Q 5/02* | (2006.01) |
| *A61Q 5/12* | (2006.01) |

(52) U.S. Cl.
CPC ................ *A61K 8/19* (2013.01); *A61K 8/362* (2013.01); *A61K 8/365* (2013.01); *A61K 8/368* (2013.01); *A61K 8/42* (2013.01); *A61K 8/442* (2013.01); *A61K 8/463* (2013.01); *A61K 8/604* (2013.01); *A61K 8/86* (2013.01); *A61K 8/894* (2013.01); *A61K 8/922* (2013.01); *A61Q 5/004* (2013.01); *A61Q 5/02* (2013.01); *A61Q 5/12* (2013.01)

(58) Field of Classification Search
None
See application file for complete search history.

(56) References Cited

U.S. PATENT DOCUMENTS

| | | | | |
|---|---|---|---|---|
| 6,231,843 B1 * | 5/2001 | Hoelzel | ................. | A61K 8/365 424/70.1 |
| 2009/0068136 A1 * | 3/2009 | Beumer | ................... | A61K 8/88 424/70.16 |

FOREIGN PATENT DOCUMENTS

| | | |
|---|---|---|
| CN | 106420499 A | 2/2017 |
| FR | 2937539 A1 | 4/2010 |

OTHER PUBLICATIONS

Jegou et al. English translation of FR 2937539 A1; accessed Oct. 3, 2018 (Year: 2010).*

* cited by examiner

*Primary Examiner* — Nicole P Babson
(74) *Attorney, Agent, or Firm* — Lorenz & Kopf, LLP

(57) ABSTRACT

A hair treatment agent for reducing and/or preventing the bleeding out and/or fading of artificially produced hair colors is provided herein. The hair treatment agent has a pH value in the range of from about 4 to about 5. The hair treatment agent includes, relative to the total amount of the hair treatment agent, from about 0.01 to about 10% by weight of a lanthanum and/or lanthanide salt, at least one anionic surfactant selected from the group of alkyl (ether) sulfates, sulfosuccinates, ether carboxylic acids, N-acylamino acids having 8 to 24 C atoms in the acyl group, (acyl) isethionates having 8 to 24 C atoms in the acyl group, and mixtures of these surfactants, and from about 0.01 to about 10% by weight of an organic acid selected from the group of maleic acid, lactic acid, acetic acid, propanoic acid, amino acids, and mixtures thereof.

20 Claims, No Drawings

STABLE COLOR-PROTECTING HAIR TREATMENT AGENT COMPRISING LANTHANIDE SALT

CROSS-REFERENCE TO RELATED APPLICATION

This application claims priority to German Patent Application No. 10 2016 210 809.3, filed Jun. 16, 2016, which is incorporated herein by reference in its entirety.

TECHNICAL FIELD

The present application relates to a hair treatment agent for reducing and/or preventing the bleeding out and/or fading of artificially produced hair colors, with a lanthanide salt and an anionic surfactant.

BACKGROUND

Products for altering the natural color of hair play a prominent role in hair cosmetics. Distinctions are made between permanent, semipermanent, and temporary color systems, which are based on chemical and/or natural dyes. Hair colors artificially produced by permanent, semipermanent, or temporary color systems have a drawback, however, in that these hair colors can undergo undesirable changes, e.g., during or after hair cleaning.

"Undesirable changes" refers here to fading or bleeding, as well as the loss of color brilliance of the shade of color of the hair obtained from the respective dyeing. Environmental impacts and/or the effects of the Sun can further intensify these changes.

There is therefore a need for hair treatment agents with which artificially produced hair colors can be better stabilized.

Hair treatment agents for protecting artificially produced hair colors or methods for stabilizing artificially produced hair colors are known in principle. FR 2937539 A1 discloses the use of lanthanide salts in hair treatment agents for protecting against washing out of artificially produced hair colors.

Lanthanide salt-containing hair treatment agents are often difficult to produce stably. The storage stability of lanthanide salt-containing hair treatment agents may also represent a problem.

The present disclosure addresses the problem of providing a (storage) stable hair treatment agent comprising lanthanide salt, with which the adherence of dyes to the hair fibers can be intensified and thus fastness of the artificially produced hair color can be obtained.

BRIEF SUMMARY

A hair treatment agent for reducing and/or preventing the bleeding out and/or fading of artificially produced hair colors is provided herein. The hair treatment agent has a pH value in the range of from about 4 to about 5. The hair treatment agent includes, relative to the total amount of the hair treatment agent, from about 0.01 to about 10% by weight of a lanthanum and/or lanthanide salt. The hair treatment agent further includes, relative to the total amount of the hair treatment agent, at least one anionic surfactant selected from the group of alkyl (ether) sulfates, sulfosuccinates, ether carboxylic acids, N-acylamino acids having 8 to 24 C atoms in the acyl group, (acyl) isethionates having 8 to 24 C atoms in the acyl group, and mixtures of these surfactants. The hair treatment agent also includes, relative to the total amount of the hair treatment agent, from about 0.01 to about 10% by weight of an organic acid selected from the group of maleic acid, lactic acid, acetic acid, propanoic acid, amino acids, and mixtures thereof.

A method for reducing and/or preventing bleeding out and/or fading of artificially produced hair color is also provided herein. The method includes applying a hair treatment agent to the dyed hair. The method further includes allowing the agent to agent for a period of at least about 5 seconds. The method also includes rinsing out the agent with water. The hair treatment agent includes, relative to the total amount of the hair treatment agent, from about 0.01 to about 10% by weight of lanthanide salt. The hair treatment agent further includes, relative to the total amount of the hair treatment agent, at least one anionic surfactant selected from the group of alkyl (ether) sulfates, sulfosuccinates, ether carboxylic acids, N-acylamino acids having 8 to 24 C atoms in the acyl group, (acyl) isethionates having 8 to 24 C atoms in the acyl group, and mixtures of these surfactants. The hair treatment agent also includes, relative to the total amount of the hair treatment agent, from about 0.01 to about 10% by weight of an organic acid selected from the group of maleic acid, lactic acid, acetic acid, propanoic acid, amino acids, and mixtures thereof.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

It has been found that a hair treatment agent that, in addition to an anionic surfactant and a lanthanide salt, also contains a selected organic acid is ideally suited therefor.

A first subject matter as contemplated herein is therefore a hair treatment agent for reducing and/or preventing the bleeding out and/or fading of artificially produced hair colors with a pH value in the range of from about 4 to about 5, containing—relative to the total amount of hair treatment agent— a) from about 0.01 to about 10% by weight a lanthanide salt;
b) at least one anionic surfactant selected from the group consisting of alkyl (ether) sulfates, sulfosuccinates, ether carboxylic acids, N-acylamino acids having 8 to 24 C atoms in the acyl group, (acyl) isethionates having 8 to 24 C atoms in the acyl group, and mixtures of these surfactants; and
c) from about 0.01 to about 10% by weight an organic acid selected from the group consisting of maleic acid, lactic acid, acetic acid, propanoic acid, amino acids, and mixtures thereof.

Suitable hair treatment agents are preferably understood to mean hair cleaning agents such as shampoos, hair care agents such as hair conditioners, rinses or hair care sprays, and hair styling agents such as hair gels, hair sprays, or hair waxes. Very especially preferably, the hair treatment agent is a shampoo.

The hair treatment agents necessarily contain a lanthanide salt.

The lanthanides are a group of similar elements. The lanthanide series includes lanthanum and the fourteen elements that follow in the periodic table of elements: cerium, praseodymium, neodymium, promethium, samarium, europium, gadolinium, terbium, dysprosium, holmium, erbium, thulium, ytterbium, and lutetium.

Especially preferred lanthanide salts include lanthanum salts, europium salts, gadolinium salts, ytterbium salts, erbium salts, and mixtures thereof. It is especially preferable for the hair treatment agent to contain at least one lanthanum salt.

The lanthanide salts used are at least slightly soluble in water, preferably readily water-soluble. A poorly water-soluble lanthanide salt is understood within the scope of the present application to mean salts that have a solubility at from about 15° C. to about 25° C. of from about 10 to about 33 g per liter of water. A readily water-soluble lanthanide salt is understood within the scope of the present application to mean salts that have a solubility at from about 15° C. to about 25° C. of at least 100 g per liter of water.

In an especially preferred embodiment, the hair treatment agents contain lanthanum chloride, lanthanum triflate, lanthanum sulfate, lanthanum nitrate, lanthanum lactate, lanthanum citrate, lanthanum salicylate, europium triflate, gadolinium triflate, ytterbium triflate, and/or erbium sulfate as the lanthanide salt. In a very especially preferably embodiment, the hair treatment agent contains lanthanum chloride as the lanthanide salt. In an exceptionally preferred embodiment of the hair treatment agent, the lanthanide salt is lanthanum chloride.

The hair treatment agents preferably contain—relative to the weight thereof—from about 0.1 to about 7.5% by weight, more preferably from about 0.5 to about 5% by weight lanthanide salt, preferably lanthanum chloride.

As a second essential ingredient, the hair treatment agents contain a selected anionic surfactant.

To the group of the selected anionic surfactants belong alkyl (ether) sulfates, sulfosuccinates, ether carboxylic acid, acyl glutamate and/or (acyl) isethionates each having 8 to 24 C atoms in the acyl group, and mixtures of these surfactants. Examples of preferred anionic surfactants include:

ether carboxylic acids of the formula R—O—(CH$_2$—CH$_2$)$_x$—CH$_2$—COOH, in which R is a linear or branched, saturated or unsaturated alkyl group having 8 to 30 C atoms and x=0 or 1 to 16;
N-acylamino acids having 8 to 24 C atoms in the acyl group;
(acyl) isethionates having 8 to 24 C atoms in the acyl group;
sulfosuccinic acid mono- and/or dialkyl esters having 8 to 24 C atoms in the alkyl group and sulfosuccinic acid monoalkyl polyoxyethyl esters having 8 to 24 C atoms in the alkyl group and 1 to 6 oxyethyl groups; and/or
alkylsulfate and/or alkyl polyglycol ether sulfate salts of the formula R—(OCH$_2$—CH$_2$)$_x$—OSO$_3$—X$^+$, in which R preferably signifies a linear or branched, saturated or unsaturated alkyl group having 8 to 30 C atoms, x signifies to the number 0 or 1 to 12, and X signifies an alkali, alkaline earth, ammonium, or alkanolamine ion.

Especially preferred anionic surfactants are straight-chained or branched alkyl ether sulfates of the aforementioned formula that contain an alkyl residue having 8 to 18, in particular, 10 to 16 C atoms, and 1 to 6, in particular, 2 to 4 ethylene oxide units. Especially preferred are the sodium, magnesium, and/or triethanolamine salts of linear or branched lauryl, tridecyl, and/or myristyl sulfates that have a degree of ethoxylation of 2 to 4.

If manufactured as a hair shampoo, the hair treatment agent preferably contains at least one anionic surfactant at a preferred proportion by weight of from about 0.5 to about 20% by weight, more preferably from about 1 to about 15, and especially preferably from about 2 to about 12% by weight, wherein the amounts are set forth with reference to the total weight of the hair treatment agent.

As a third essential ingredient, the hair treatment agents contain—relative to the weight thereof—from about 0.01 to about 10% b weight a selected organic acid.

The organic acid is selected from the group consisting of maleic acid, lactic acid, acetic acid, propanoic acid, amino acids, and mixtures thereof. Suitable amino acids include glycine, glutamic acid, arginine, and/or aspartic acid. It is especially preferable to use lactic acid and/or maleic acid as the organic acid.

The hair treatment agents preferably contain the organic acid in an amount of from about 0.1 to about 5% by weight, especially preferably from about 0.5 to about 3% by weight, in each case relative to the weight of the ready-to-use hair treatment agent.

The organic acids are serve, in particular, to adjust the pH value of the hair treatment agent to a value between about 4 and about 5. It has surprisingly been shown that using mineral acids such as sulfuric acid, hydrochloric acid, or nitric acid alone does not lead to stable lanthanide salt-containing hair treatment agents. In combination with an amino acid, preferably glycine, glutamic acid, arginine, and/or aspartic acid, HCl can be used to adjust the pH value from about 4 to about 5.

In a preferred embodiment, the hair treatment agent has a pH value in the range of from about 4.5 to about 5.

It has been shown that using an organic acid in combination with a lanthanide salt endows the hair treatment agents with excellent properties. Thus, there is extremely little discoloration of the artificially produced hair color after multiple treatments.

It has been found that it is especially effective, and the change in color for the artificially produced color after a plurality of cleanings is especially low when the hair treatment agents contain lanthanum chloride and maleic acid or lanthanum chloride and lactic acid.

The hair treatment agent furthermore preferably contains an aqueous or aqueous-alcoholic carrier. An aqueous carrier contains at least 50% by weight water. Aqueous-alcoholic carriers are understood as contemplated herein to mean aqueous solutions containing from about 3 to about 70% by weight a C$_2$-C$_6$ alcohol, in particular, ethanol, propanol, isopropanol, butanol, isobutanol, tert-butanol, n-pentanol, iso-pentanols, n-hexanol, iso-hexanols, glycol, glycerol, 1,2-pentanediol, 1,5-pentanediol, 1,2-hexandeiol, or 1,6-hexanediol. The agents may additionally contain other organic solvents, e.g., methoxybutanol, benzyl alcohol, ethyl diglycol, or 1,2-propylene glycol. All water-soluble organic solvents are preferred.

The hair treatment agents may in principle be used on hair that has been dyed with permanent, semipermanent, or temporary hair color. However, temporary hair colors are meant to be washed out and/or faded with time, for which reason the hair treatment agent is especially suitable for use on hair that have been colored with permanent or oxidative hair dyes.

The hair treatment agents may, in addition to the aforementioned ingredients, also contain other ingredients that are common in the respective agents.

In addition to an anionic surfactant, the hair treatment agent may contain a cationic surfactant. The cationic surfactants comprise, in particular, quaternary ammonium compounds, Esterquats, and/or amidoamines.

Preferred quaternary ammonium compounds are ammonium halides, in particular, chlorides or bromides, such as alkyltrimethylammonium chlorides, dialkyldimethylammonium chlorides, and trialkylmethylammonium chlorides, for example, cetyl trimethyl ammonium chloride, stearyl trimethyl ammonium chloride, distearyl dimethyl ammonium chloride, lauryl dimethyl ammonium chloride, lauryl dimethyl benzyl ammonium chloride, and tricetyl methyl ammonium chloride, as well as the imidazolium compounds known under the INCI designations Quaternium-27, Quaternium-83, and Quaternium-87. The alkyl chains of the above-mentioned surfactants preferably have 10 to 18 carbon atoms.

Esterquats entail substances that contain both at least one ester function and at least one quaternary ammonium group as a structural element. Preferred Esterquats are quaternized ester salts of fatty acids with triethanolamine, quaternized ester salts of fatty acids with diethanol alkyl amines, and quaternized ester salts of fatty acids with 1,2-dihydroxypropyl dialkyl amines. Specific examples are methyl-N-(2-hydroxyethyl)-N,N-di(talgacyloxyethyl)ammonium compounds, bis-(palmitoyloxyethyl)hydroxyethyl methyl ammonium compounds, methyl-N,N-bis(stearoyloxyethyl)-N-(2-hydroxyethyl)ammonium compounds, methyl-N,N-bis(cocoyloxyethyl)-N-(2-hydroxyethyl)ammonium compounds, or N,N-dimethyl-N,N-di(talgacyloxyethyl) ammonium compounds Such products are sold, for example, under the names Stepantex®, Dehyquart®, Armocare®, and Quartamin®.

Alkylamidoamines are normally prepared by the amidation of natural or synthetic fatty acids and fatty acid fractions with dialkylaminoamines. An especially suitable compound of this substance group is stearamidopropyl dimethylamine, commercially available under the trade name Tegoamid® S 18.

The amount of cationic surfactant is preferably at most about 2% by weight, relative to the total weight of the hair treatment agent.

The effectiveness of the hair treatment agents can be still further increased when a specific hair-conditioning active ingredient is added thereto. In particular, the color brilliance of the artificially produced hair color can be stabilized and maintained thereby. The hair treatment agents therefore additionally contain at least one hair-conditioning active ingredient at a proportion by weight of from about 0.01 to about 10% by weight to the total weight of the hair treatment agent. Suitable hair-conditioning active ingredients are understood to mean: preferably cationic care polymers; natural, mineral, or synthetic oil, fat, or wax components; vitamins; and/or protein hydrolyzates. Using a cationic polymer, preferably a cationic polysaccharide, and/or a vegetable oil and/or a silicone as the hair-conditioning active ingredient makes it possible not only to favorably stabilize the color brilliance of the hair, but also to improve the haptic properties, such as the grip and the softness of the dyed hair.

Further suitable ingredients include non-ionic surfactants, amphoteric/zwitterionic surfactants, non-ionic polymers, anionic polymers, amino acids, oligopeptides, vitamins, provitamins, vitamin precursors, betaines, bioquinons, purine (derivatives), taurine (derivatives), L-carnitine (salts), panthenol, pantothenic acid, 2-furanones, 2-furanone derivatives, ectoine, allantoin, plant extracts, ester oils, UV light protection filters, structuring agents, thickening agents, electrolytes, pH adjusting agents, swelling agents, dyes, anti-dandruff ingredients, complexing agents, opacifiers, pearlescing agents, pigments, stabilizing agents, propellants, antioxidants, perfume oils, and/or preservatives.

Preferred hair treatment agents are characterized as follows:
  from about 0.1 to 7 about 5% by weight a lanthanum salt;
  from about 0.5 to about 20.0% by weight at least one anionic surfactant selected from the group consisting of alkyl (ether) sulfates, sulfosuccinates, ether carboxylic acids, N-acylamino acids having 8 to 24 C atoms in the acyl group, (acyl) isethionates having 8 to 24 C atoms in the acyl group, and mixtures of these surfactants;
  from about 0.1 to about 5.0% by weight an organic acid selected from the group consisting of maleic acid, lactic acid, acetic acid, propanoic acid, amino acids, and mixtures thereof; and
  a pH value in the range of from about 4 to about 5.

Further preferred hair treatment agents are characterized as follows:
  from about 0.5 to about 5.0% by weight a lanthanum salt, including lanthanum chloride;
  from about 0.5 to about 20.0% by weight at least one anionic surfactant selected from the group consisting of alkyl (ether) sulfates, sulfosuccinates, ether carboxylic acids, N-acylamino acids having 8 to 24 C atoms in the acyl group, (acyl) isethionates having 8 to 24 C atoms in the acyl group, and mixtures of these surfactants;
  from about 0.1 to about 5.0% by weight an organic acid selected from the group consisting of maleic acid, lactic acid, acetic acid, propanoic acid, amino acids, and mixtures thereof; and
  a pH value in the range of from about 4 to about 5.

Still further preferred hair treatment agents are characterized as follows:
  from about 0.5 to about 5.0% by weight a lanthanum salt, including lanthanum chloride;
  from about 0.5 to about 20.0% by weight at least one anionic surfactant selected from the group consisting of alkyl (ether) sulfates, sulfosuccinates, ether carboxylic acids, N-acylamino acids having 8 to 24 C atoms in the acyl group, (acyl) isethionates having 8 to 24 C atoms in the acyl group, and mixtures of these surfactants;
  from about 0.1 to about 5.0% by weight an organic acid selected from the group consisting of maleic acid, lactic acid, acetic acid, propanoic acid, amino acids, and mixtures thereof;
  from about 0.01 to about 10% by weight at least one cationic polysaccharide; and
  a pH value in the range of from about 4 to about 5.

Within this embodiment, hair treatment agents characterized as follows are extremely preferred:
  from about 0.5 to about 5.0% by weight a lanthanum salt, which is lanthanum chloride;
  from about 0.5 to about 20.0% by weight at least one alkylsulfate and/or alkyl polyglycol ether sulfate salt of the formula $R-(OCH_2-CH_2)_x-OSO_3-X^+$, in which R preferably signifies a linear or branched, saturated or unsaturated alkyl group having 8 to 30 C atoms, x signifies to the number 0 or 1 to 12, and X signifies an alkali, alkaline earth, ammonium, or alkanolamine ion;
  from about 0.5 to about 3.0% by weight an organic acid selected from the group consisting of maleic acid, lactic acid, and mixtures thereof;
  from about 0.01 to about 10% by weight at least one of the cationic polysaccharides known under the INCI designations Polyquaternium-10, Guar Hydroxypropyltrimonium Chloride, and/or Polyquaternium-67; and
  a pH value in the range of from about 4.5 to about 5.

Also preferred hair treatment agents are those that—instead of the cationic polysaccharide—contain a natural, mineral, or synthetic oil, fat, or wax component, in particular, from about 0.01 to about 10% by weight at least one vegetable oil and/or a silicone, as a hair-conditioning active ingredient.

Another subject matter as contemplated herein is a method for reducing and/or preventing bleeding out and/or fading of artificially produced hair colors, comprising the following steps:
i. applying a hair treatment agent to the—preferably wet—dyed hair,
ii. allowing the agent to agent for a period of at least 5 seconds,
iii. optionally: rinsing out the composition with water, characterized in that
the hair treatment agent contains, relative to the weight thereof:
d) from about 0.01 to about 10% by weight a lanthanide salt;
e) at least one anionic surfactant selected from the group consisting of alkyl (ether) sulfates, sulfosuccinates, ether carboxylic acids, N-acylamino acids having 8 to 24 C atoms in the acyl group, (acyl) isethionates having 8 to 24 C atoms in the acyl group, and mixtures of these surfactants; and
f) from about 0.01 to about 10% by weight an organic acid selected from the group consisting of maleic acid, lactic acid, acetic acid, propanoic acid, amino acids, and mixtures thereof.

In a first preferred embodiment, the method comprises the following steps:
i. applying a shampoo—as a hair treatment agent—to the wet dyed hair,
ii. allowing the shampoo to act for a period of from about 5 seconds to about 5 minutes,
iii. rinsing out the shampoo with water.

Another subject matter as contemplated herein is the use of the hair treatment agent to reduce and/or prevent bleeding out and/or fading of artificially produced hair colors and/or improve the color intensity and/or color fidelity.

Examples

The following hair treatment agents were prepared (quantities refer here to % by weight):

Color-Protecting Shampoos

|  | Shampoo 1 | Shampoo 2 | Shampoo 3 |
|---|---|---|---|
| Sodium laureth sulfate | 12.5 | 14.5 | 16.5 |
| Cocamidopropyl betaine | 4.0 | 4.0 | 4.0 |
| Disodium cocoamphodiacetate | 2.0 | 2.0 | 2.0 |
| PEG-12 dimethicone | 0.5 | 0.5 | 0.5 |
| PEG-7 glyceryl cocoate | 0.5 | 0.5 | 0.5 |
| Polyquaternium-10 | 0.3 | 0.3 | 0.3 |
| Hydrogenated castor oil | 0.6 | 0.6 | 0.6 |
| Sodium benzoate | 0.5 | 0.5 | 0.5 |
| Lanthanum chloride | 3.0 | 3.0 | 3.0 |
| Maleic acid | — | 2.0 | 2.0 |
| Lactic acid | 2.0 | — | — |
| NaOH for adjusting the pH | + | + | + |
| Water | up to 100 | up to 100 | up to 100 |
| pH value | 4.5 | 4.5 | 4.5 |

The shampoos 1 to 3 were produced by employing conventional production methods. The formulations, after preparation, were homogeneous and remained storage-stable over several weeks thereafter.

Shampoos having a pH value above or below the range of from about 4 to about 5 were not stable.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

What is claimed is:
1. A shampoo having a pH of about 4 to about 5 and consisting of:
sodium laureth sulfate present in an amount of 12.5 to 16.5 weight percent based on a total weight of said shampoo;
cocamidopropyl betaine present in an amount of 4 weight percent based on a total weight of said shampoo;
disodium cocoamphodiacetate present in an amount of 2 weight percent based on a total weight of said shampoo;
PEG-12 dimethicone present in an amount of 0.5 weight percent based on a total weight of said shampoo;
PEG-7 glyceryl cocoate present in an amount of 0.5 weight percent based on a total weight of said shampoo;
polyquaternium-10 present in an amount of 0.3 weight percent based on a total weight of said shampoo;
hydrogenated castor oil present in an amount of 0.6 weight percent based on a total weight of said shampoo;
sodium benzoate present in an amount of 0.5 weight percent based on a total weight of said shampoo;
lanthanum chloride present in an amount of 3 weight percent based on a total weight of said shampoo;
maleic acid and/or lactic acid present in an amount of 2 weight percent based on a total weight of said shampoo;
NaOH for adjusting the pH; and
water present in an amount such that a total weight of all components is 100 weight percent.
2. The shampoo of claim 1 having a pH of 4.5.
3. The shampoo of claim 2 wherein the maleic acid is present in an amount of 2 weight percent based on a total weight of said shampoo.
4. The shampoo of claim 2 wherein the lactic acid is present in an amount of 2 weight percent based on a total weight of said shampoo.
5. The shampoo of claim 1 wherein the maleic acid is present in an amount of 2 weight percent based on a total weight of said shampoo.
6. The shampoo of claim 1 wherein the lactic acid is present in an amount of 2 weight percent based on a total weight of said shampoo.
7. The shampoo of claim 1 wherein the sodium laureth sulfate is present in an amount of 12.5 weight percent based on a total weight of said shampoo.

8. The shampoo of claim 7 having a pH of 4.5.

9. The shampoo of claim 8 wherein the lactic acid is present in an amount of 2 weight percent based on a total weight of said shampoo.

10. The shampoo of claim 7 wherein the lactic acid is present in an amount of 2 weight percent based on a total weight of said shampoo.

11. The shampoo of claim 1 wherein the sodium laureth sulfate is present in an amount of 14.5 weight percent based on a total weight of said shampoo.

12. The shampoo of claim 11 having a pH of 4.5.

13. The shampoo of claim 12 wherein the maleic acid is present in an amount of 2 weight percent based on a total weight of said shampoo.

14. The shampoo of claim 11 wherein the maleic acid is present in an amount of 2 weight percent based on a total weight of said shampoo.

15. The shampoo of claim 1 wherein the sodium laureth sulfate is present in an amount of 16.5 weight percent based on a total weight of said shampoo.

16. The shampoo of claim 15 having a pH of 4.5.

17. The shampoo of claim 16 wherein the maleic acid is present in an amount of 2 weight percent based on a total weight of said shampoo.

18. The shampoo of claim 15 wherein the maleic acid is present in an amount of 2 weight percent based on a total weight of said shampoo.

19. A method for reducing and/or preventing bleeding out and/or fading of artificially produced hair color, the method comprising:

i. applying the shampoo of claim 1 to dyed hair, ii. allow the shampoo to remain for a period of at least about 5 seconds, and optionally: rinsing out the shampoo with water.

20. The method of claim 19, wherein the dyed hair is wet during application of the shampoo.

* * * * *